United States Patent
Haindl

(10) Patent No.: US 11,318,071 B2
(45) Date of Patent: May 3, 2022

(54) PLASTER FOR SECURING A TUBE

(71) Applicant: GBUK Group Limited, Selby (GB)

(72) Inventor: Cornelia Haindl, Selby (GB)

(73) Assignee: GBUK Group Limited, Selby (GB)

( * ) Notice: Subject to any disclaimer, the term of this patent is extended or adjusted under 35 U.S.C. 154(b) by 251 days.

(21) Appl. No.: 16/779,854

(22) Filed: Feb. 3, 2020

(65) Prior Publication Data

US 2020/0281818 A1    Sep. 10, 2020

(30) Foreign Application Priority Data

Feb. 11, 2019  (GB) ..................................... 1901825

(51) Int. Cl.
  *A61J 15/00*  (2006.01)
  *A61M 25/02*  (2006.01)

(52) U.S. Cl.
  CPC ....... *A61J 15/0057* (2013.01); *A61J 15/0003* (2013.01); *A61M 25/02* (2013.01); *A61M 2025/0226* (2013.01); *A61M 2025/0266* (2013.01)

(58) Field of Classification Search
  CPC .. A61J 15/0057; A61J 15/0003; A61M 25/02; A61M 2025/0226; A61M 2025/0213; A61M 2025/022; A61M 2025/0246; A61M 2025/0253; A61M 5/14248; A61M 2205/586; A61M 2025/026; A61F 13/02; A61F 2013/00289; A61F 2013/00297; A61F 2013/0057
  See application file for complete search history.

(56) References Cited

U.S. PATENT DOCUMENTS

| 4,336,806 A * | 6/1982 | Eldridge, Jr. ......... A61M 25/02 128/DIG. 26 |
| 4,966,605 A * | 10/1990 | Thieler ................ A61B 17/085 606/215 |
| 5,153,040 A * | 10/1992 | Faasse, Jr. ............ A61F 13/023 428/131 |
| D755,962 S * | 5/2016 | Adams ........................ D24/128 |
| 2006/0041233 A1 | 2/2006 | Bowen |

(Continued)

FOREIGN PATENT DOCUMENTS

EP    2837401 A2    2/2015

OTHER PUBLICATIONS

Extended European Search Report in corresponding European Patent Application No. 20155129.8, dated May 20, 2020.

(Continued)

*Primary Examiner* — Bhisma Mehta
*Assistant Examiner* — Phoebe Anne Staton
(74) *Attorney, Agent, or Firm* — Dergosits & Noah LLP; Todd A. Noah

(57) ABSTRACT

The invention provides a plaster for use in securing a tube to a patient. The plaster comprises a top layer having an upper surface, a lower surface, and a pull tab. The plaster also comprises a base layer having an upper surface, and a lower surface. At least a portion of the lower surface of the top layer or the upper surface of the base layer is provided with an adhesive for adhering the plaster to the tube. The lower surface of the base layer is provided with an adhesive for adhering the plaster to the patient. The top layer includes a hinge about which the pull tab can be oriented away from the skin of the patient.

15 Claims, 3 Drawing Sheets

(56) References Cited

U.S. PATENT DOCUMENTS

| | | | |
|---|---|---|---|
| 2007/0073211 A1* | 3/2007 | Propp | A61M 25/02 |
| | | | 602/57 |
| 2008/0195050 A1 | 8/2008 | Dickert et al. | |
| 2012/0083743 A1* | 4/2012 | Kyvik | A61M 25/02 |
| | | | 604/180 |
| 2013/0150796 A1* | 6/2013 | Souza | A61F 13/0259 |
| | | | 604/180 |
| 2016/0193117 A1* | 7/2016 | Geosits | A61J 15/0061 |
| | | | 604/516 |
| 2018/0161543 A1* | 6/2018 | Burkholz | A61M 25/02 |

OTHER PUBLICATIONS

Search Report from Great Britain Patent Application No. 1901825.8, dated Jul. 8, 2019.

* cited by examiner

PLASTER FOR SECURING A TUBE

CLAIM OF PRIORITY

This application claims priority to United Kingdom Patent Application No. 1901825.8, filed Feb. 11, 2019, the content of which is hereby incorporated by reference in its entirety.

FIELD OF THE INVENTION

The present invention relates generally to a plaster for use in securing a tube to a patient.

BACKGROUND TO THE INVENTION

Medical and surgical tubes or lines are used to administer fluids to, or remove fluids from, a patient. Non-limiting examples include nasal feeding tubes, catheters, intravenous (IV) tubes, perfusion tubes, aspiration systems and drainage systems.

Nasal feeding tubes are non-surgical and placed temporarily through the nose and into the stomach or intestine.

Nasogastric intubation is a medical process in which a nasogastric (NG) feeding tube is inserted through the nose, down the oesophagus and into the stomach.

Nasojejunal intubation is a medical process in which a nasojejunal (NJ) feeding tube is inserted through the nose, down the oesophagus, through the stomach and into the first portion (jejunum) of the small intestine.

Nasoduodenal intubation is a medical process in which a nasoduodenal (ND) feeding tube is inserted through the nose, down the oesophagus, through the stomach and into the second portion (duodenum) of the small intestine.

The NG, NJ or ND tube is securely retained in place using a fixation plaster or adhesive tape adhered to the nose. This prevents the tube being misplaced or falling out accidentally.

Existing plasters for fixing NG, NJ, ND tubes are difficult to manually handle, this is particularly so when the user is wearing gloves. Furthermore, existing plasters do not enable a user to readily visualise if the patient is having an allergic reaction to the plaster, or an infection is developing under the plaster, without having to repeatedly remove at least part of the plaster. The tube often applies pressure where it touches the patient's skin, which can lead to skin injury and the development of pressure ulcers.

There is therefore a need for plaster that can be used to secure tubes to a patient and which addresses the problems outlined above.

SUMMARY OF THE INVENTION

According to a first aspect of the invention there is provided a plaster for use in securing a tube to a patient, the plaster comprising:
  a top layer having an upper surface, a lower surface, and a pull tab, and
  a base layer having an upper surface, and a lower surface,
  wherein at least a portion of the lower surface of the top layer or the upper surface of the base layer is provided with an adhesive for adhering the plaster to the tube,
  wherein the lower surface of the base layer is provided with an adhesive for adhering the plaster to the patient, and
  wherein the top layer includes a hinge about which the pull tab can be oriented away from the skin of the patient.
  A tube is retained between the top layer and the base layer of the plaster.

The pull tab provided on the top layer facilitates the user positioning the top layer of the plaster relative to the base layer of the plaster when securing or removing a tube.

In some constructions, the pull tab extends beyond an outer perimeter of the base layer.

The ability to be able to orient the pull tab of the top layer away from the skin of the patient is therefore advantageous because this will minimise any irritation caused to the skin. This is particularly advantageous for plasters in which the pull tab is made of a relatively rigid plastic that will not readily conform to the contours of the skin. This is also particularly advantageous for plasters in which the pull tab is made of a plastic that is likely to curl, such that a blunt edge of the pull tab rests against the skin of the patient and causes irritation.

In some constructions, the hinge that enables the pull tab to be oriented away from the patient's skin is defined by a line of weakness within the material from which the top layer is formed. For example, the line of weakness may be intermittent, and may take the form of a line of perforations. In other constructions, the line of weakness may be continuous and take the form of a line of thinned material.

Optionally, the pull tab can be torn from the plaster by the action of the user tearing along the hinge. Accordingly, the pull tab is separable from, and hence a removable and disposable component of the plaster.

Optionally, the pull tab on the top layer is made of a thicker material than the remainder of the top layer.

In some constructions, the base layer comprises a grip tab by which the base layer can be gripped to allow the top layer and/or a protective backing layer provided on the base later to be readily peeled away from the base layer. A lower surface of the grip tab may be adhesive free.

Optionally, the grip tab on the base layer is made of a thicker material than the remainder of the base layer.

In some constructions, prior to orientation away from the patient's skin the pull tab overlies and extends beyond the grip tab of the base layer.

The top layer and the base layer may be formed from a single sheet of material that is folded over to provide the two layers.

In other constructions, the top layer and the base layer may be provided as two separate sheets of material that are then secured together at or near a perimeter edge. For example, a portion of the top layer and the base layer may be adhered together by physical or chemical means. This may include the use of an adhesive or heat-bonding.

In some constructions, the top layer may include a first portion secured to the base layer, a second portion for securing about the tube, and a hinge which enables the second portion to be oriented relative to the first portion when the top layer is peeled away from the base layer.

In some constructions, the plaster further comprises a cushioning material sandwiched between the top layer and the base layer. This cushioning material provides a cushioning effect against the weight of a nasal feeding tube on the skin. This is particularly advantageous for neonatal patients in which the skin is particularly delicate and prone to bruising and irritation.

The cushioning material may comprise a sheet of silicone. The plaster may be provided to the user with the cushioning material already secured to the base layer. Alternatively, the cushioning material may be provided as an optional feature, capable of being adhered to the upper surface of the base layer, if required. The lower surface of the cushioning material may be provided with an adhesive.

Optionally, an upper surface of the cushioning material may be provided with an adhesive. This enables the cushioning material to be adhered both to the surface of the tube, and to the lower surface of the top layer.

Prolonged fixation of a plaster on the skin may result in skin irritation and/or infection. This is often the case if moisture (e.g., sweat) is accumulates between the skin and the underside of the plaster. Irritation may also be caused by an allergic reaction to the materials that the plaster is manufactured from, for example the type of adhesive used. It is therefore advantageous if any skin irritation and/or infection is detected early, for the comfort and well-being of the patient. Accordingly, in some constructions of the plaster the top layer, base layer and (if used) the cushioning material is substantially transparent. An additional advantage of this is that the plaster is discreet.

In some constructions of the plaster, the outer profile of the plaster is symmetrical. This ensures that the plaster is compatible for use on the right and left cheeks.

The outer profile of the plaster is also ergonomic, ensuring that the plaster is capable of fitting closely under the nose.

Removable protective layers may be provided on any adhesive surface, with the protective layers being removed at the time of use.

In some constructions, the tube is a nasogastric tube, nasojejunal tube or a nasoduodenal tube.

According to a second aspect of the invention there is provided a method of securing a tube to a patient comprising the steps of:
 (a) providing a plaster as described herein,
 (b) securing the lower surface of the base layer to the skin of the patient,
 (c) grasping the pull tab on the top layer and peeling the top layer away from the base layer,
 (d) placing a tube over the upper surface of the base layer,
 (e) securing the top layer over the tube,
 (f) bringing the lower surface of top layer into contact with the upper surface of the base layer, and
 (g) moving the pull tab about the hinge to orient the pull tab away from contact with the skin of the patient.

It is not essential that step (g) is the final step in the temporal sequence outlined above. For example, the user may move the pull tab at the same time as grasping the pull tab in step (c).

In some examples of the method, the pull tab is removable such that the user may tear the pull tab away from the top layer. This may be achieved by the user tearing along the hinge.

In some examples of the method, the user may insert a cushioning material, such as a silicone sheet, between the base layer and the tube. The cushioning material may be secured to the upper surface of the base layer, by an adhesive.

According to a third aspect of the invention there is provided a kit comprising:
 a plaster comprising:
 a top layer having an upper surface, a lower surface, and a pull tab, and
 a base layer having an upper surface, and lower surface,
 wherein at least one of the lower surfaces of the top layer or the upper surface of the base layer is provided with an adhesive for adhering the plaster to a tube,
wherein the lower surface of the base layer is provided with an adhesive for adhering the plaster to a patient, and
wherein the top layer includes a hinge about which the pull tab can be oriented away from the skin of the patient, and a cushioning material for insertion between the base layer and the tube.

In some constructions of the kit, the cushioning material may comprise a sheet of silicone.

It is also envisaged that kits of plasters for use with tubes may be sold that include different sizes and/or shapes of plaster.

BRIEF DESCRIPTION OF THE FIGURES

The invention will now be described, by way of example only, with reference to the following drawings, in which.

DETAILED DESCRIPTION

Figure 1:
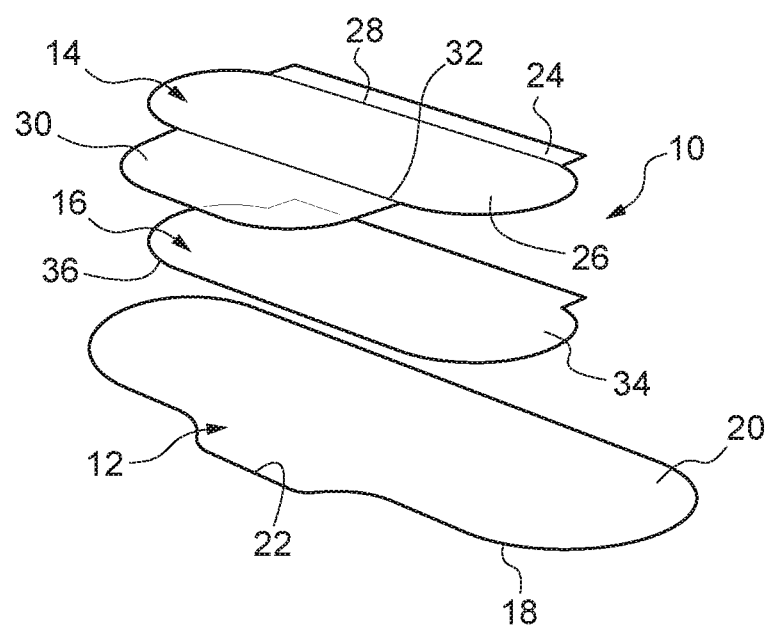
FIG. 1 shows a schematic of a construction of the plaster according to the invention in an unassembled format.
Figure 2:
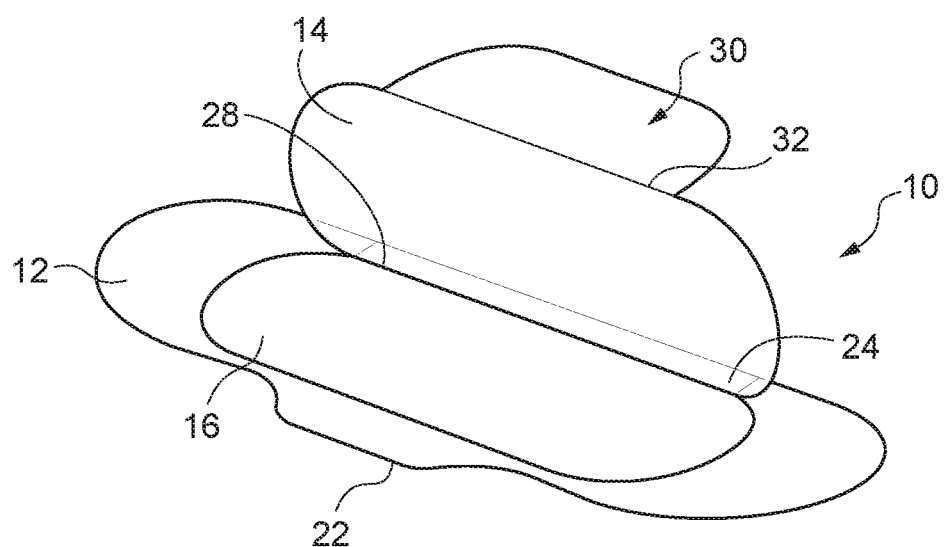
FIG. 2 shows a schematic of the plaster of FIG. 1 in an assembled format.

The plaster 10 shown in FIG. 1 and FIG. 2 includes a base layer 12 and a top layer 14. A cushioning material 16 is sandwiched between the base layer 12 and the top layer 14.

In the exemplary construction shown, the base layer 12 has lozenge-like outer profile, with curved outer edges. The base layer has a lower surface 18 and an upper surface 20. At least a part of the lower surface is provided with an adhesive for adhering the base layer to the skin of the patient.

The base layer has a grip tab 22 that extends outwardly beyond the outer lozenge-like profile of the base layer. The grip tab is in the same plane as the rest of the base layer. The grip tab 22 can be gripped by the user as the top layer 14 is being peeled away from the base layer 12. This prevents the base layer from being inadvertently peeled away from the skin, if the force required to separate the top layer from the base layer exceeds the force required to separate the base layer from the skin.

The base layer may be made of a transparent material.

The top layer 14 also has a lozenge-like outer profile with curved edges. The top layer 14 is smaller than the base layer 12.

The top layer has a first portion 24, also referred to as the base layer fixation portion 24, in the form of a strip, along which the top layer is adhered to the base layer. The top layer also includes a second portion 26, also referred to as the nasogastric tube contacting portion 26, the lower surface of which is brought into contact with the nasogastric tube. The top layer also includes a first hinge 28 located between the first portion and the second portions which enables the second portion to be oriented relative to the first portion when the top layer is peeled away from the base layer. The first hinge 28 may be formed by a line of thinned material.

The top layer also has a pull tab 30 that extends outwardly beyond the lozenge-like outer profile of the top layer. The top layer includes a second hinge 32 located between second portion 26 and the pull tab 30. The second hinge 32 may be formed by a line of thinned material. The second hinge 32 enables the pull tab to be oriented out of contact with the skin of the patient.

Prior to orientation away from the patient's skin, the pull tab 30 overlies and extends outwardly beyond the grip tab 22.

The top layer 14 may be made of a transparent material.

The cushioning material 16 also has a lozenge-like outer profile with curved edges. The dimensions of the cushioning material 16 are the same as, or substantially similar to, the dimensions of the top layer 14.

The cushioning material is sandwiched between the base layer 12 and the top layer 14. The cushioning material 16 may take the form of a silicone sheet having adhesive provided on its upper surface 34 and lower surface 36. The lower surface 36 of the cushioning material is adhered to the upper surface 20 of the base layer 12. The upper surface 34 of the cushioning material is adhered to the nasogastric tube and to the lower surface 26 of the top layer 14. In essence, the nasogastric tube (not shown) is sandwiched between the cushioning material 16 and the top layer 14.

Figure 3:
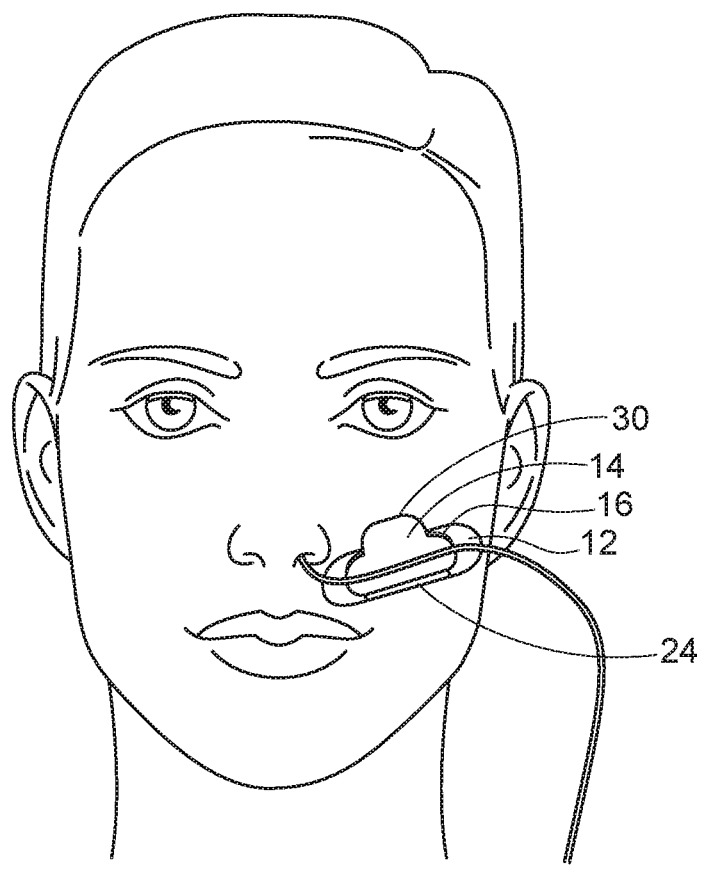
FIG. 3 shows a schematic of the plaster of FIG. 3 secured about a nasogastric tube on a patient.

FIG. 3 shows the exemplary construction of the plaster of FIGS. 1 and 2 positioned on a patient. The curved outer edge of the base layer 12 has an ergonomic shape that is designed to enable the plaster to fit closely under the nose of the patient. The symmetry of the design enables the plaster to be used on the right or left cheek of the patient.

Although the exemplary construction of the plaster shown in FIGS. 1 to 3 includes a cushioning material, this is an optional feature and accordingly this may be provided as a separate component, for use, if required. The cushioning material may be used in conjunction with the plaster in paediatric patients, in which the skin on the face is more fragile, and more prone to bruising by the weight of a nasal feeding tube.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure as defined by the claims.

What is claimed is:

1. A plaster for use in securing a tube to skin of a patient, the plaster comprising:
    a top layer having an upper surface, a lower surface, a pull tab and a hinge about which the pull tab can be oriented away from the skin of the patient, the pull tab being removable from the top layer; and
    a base layer having an upper surface and a lower surface, the lower surface of the base layer including an adhesive for adhering the plaster to the patient,
        wherein at least a portion of the lower surface of the top layer or the upper surface of the base layer is provided with an adhesive for adhering the plaster to the tube.

2. The plaster of claim 1, wherein the top layer is formed from a material having a line of weakness therein defining the hinge.

3. The plaster of claim 2, wherein the line of weakness is intermittent.

4. The plaster of claim 3, wherein the line of weakness comprises a plurality of perforations.

5. The plaster of claim 2, wherein the line of weakness is defined by a thinned region of material.

6. The plaster of claim 1, wherein prior to orientation away from the skin of the patient the pull tab overlies and extends outwardly beyond an outer perimeter of the base layer.

7. The plaster of claim 1, wherein the base layer comprises a grip tab by which the base layer can be gripped to allow the top layer to be peeled away from the base layer.

8. The plaster of claim 7, wherein the pull tab overlies and extends outwardly beyond an outer perimeter of the grip tab.

9. The plaster of claim 1, wherein the plaster further comprises a cushioning material sandwiched between the top layer and the base layer.

10. The plaster of claim 9, wherein the cushioning material is a silicone sheet.

11. The plaster of claim 10, wherein the top layer, the base layer and the cushioning material are substantially transparent.

12. The plaster of claim 1, wherein the tube is a nasogastric tube, nasojejunal tube or a nasoduodenal tube.

13. A method of securing a tube to a patient comprising the steps of:
    (a) providing a plaster of claim 1,
    (b) securing the lower surface of the base layer to a skin of the patient,
    (c) grasping the pull tab on the top layer, tearing the pull tab from the top layer and peeling the top layer away from the base layer,
    (d) placing a tube over the upper surface of the base layer,
    (e) securing the top layer over the tube,
    (f) bringing the lower surface of the top layer into contact with the upper surface of the base layer, and
    (g) moving the pull tab about the hinge to orient the pull tab away from contact with the skin of the patient.

14. The method of claim 13, wherein a cushioning material is brought into contact with the base layer.

15. A kit for use in securing a tube to skin of a patient comprising:
    a plaster having:
        a top layer having an upper surface, a lower surface, a pull tab and a hinge about which the pull tab can be oriented away from the skin of the patient, the pull tab being removable from the top layer, and
        a base layer having an upper surface and a lower surface, the lower surface of the base layer including an adhesive for adhering the plaster to the patient,
            wherein at least a portion of the lower surface of the top layer or the upper surface of the base layer is provided with an adhesive for adhering the plaster to the tube; and
    a cushioning material for insertion between the top layer and the base layer.

* * * * *